United States Patent
Shoji (10) Patent No.: US 8,741,053 B2
(45) Date of Patent: Jun. 3, 2014

(54) CALCIUM PHOSPHATE CEMENT COMPOSITION AND ITS KIT FOR BONE PROSTHESIS

(75) Inventor: Daisuke Shoji, Tokyo (JP)

(73) Assignee: Hoya Technosurgical Corporation, Tokyo (JP)

( * ) Notice: Subject to any disclaimer, the term of this patent is extended or adjusted under 35 U.S.C. 154(b) by 97 days.

(21) Appl. No.: 13/264,522

(22) PCT Filed: Apr. 16, 2010

(86) PCT No.: PCT/JP2010/056851
§ 371 (c)(1),
(2), (4) Date: Oct. 14, 2011

(87) PCT Pub. No.: WO2010/119953
PCT Pub. Date: Oct. 21, 2010

(65) Prior Publication Data
US 2012/0031305 A1    Feb. 9, 2012

(30) Foreign Application Priority Data
Apr. 17, 2009    (JP) .................................. 2009-101141

(51) Int. Cl.
*C04B 12/02*    (2006.01)

(52) U.S. Cl.
USPC .............................. 106/690; 106/691; 106/35

(58) Field of Classification Search
USPC .......................................... 106/690, 691, 35
See application file for complete search history.

(56) References Cited

U.S. PATENT DOCUMENTS

| 7,732,573 | B2 | 6/2010 | Tanaka et al. |
| 8,008,357 | B2 | 8/2011 | Shoji et al. |
| 8,039,090 | B2 | 10/2011 | Kawamura et al. |
| 2003/0180344 | A1 | 9/2003 | Wise et al. |
| 2005/0025807 | A1 | 2/2005 | Ootsuka et al. |
| 2006/0172918 | A1 | 8/2006 | Sotome et al. |
| 2009/0149634 | A1 | 6/2009 | Shoji et al. |
| 2010/0063598 | A1 | 3/2010 | Hirata et al. |
| 2010/0145468 | A1 | 6/2010 | Shoji |
| 2010/0166828 | A1 | 7/2010 | Shoji |
| 2011/0014266 | A1 | 1/2011 | Shoji |
| 2011/0033552 | A1 | 2/2011 | Shoji |
| 2011/0054630 | A1 | 3/2011 | Shoji |
| 2012/0024195 | A1 | 2/2012 | Shoji |

FOREIGN PATENT DOCUMENTS

| JP | 64-62164 | 3/1989 |
| JP | 06-030985 | 2/1994 |

(Continued)

OTHER PUBLICATIONS

International Search Report for PCT/JP2010/056851, mailed Jun. 8, 2010.

(Continued)

*Primary Examiner* — Paul Marcantoni
(74) *Attorney, Agent, or Firm* — Greenblum & Bernstein, P.L.C.

(57) ABSTRACT

A calcium phosphate cement composition kit comprising (A) a powdery agent comprising 100 parts by mass of calcium phosphate powder, and 5-50 parts by mass of a powdery apatite/collagen composite, and (B) an aqueous blending liquid; a paste-like mixture being obtained by blending the powdery agent with the aqueous blending liquid, in such a proportion that the aqueous blending liquid is 15-50 parts by mass per the total amount (100 parts by mass) of the calcium phosphate powder and the powdery apatite/collagen composite, and filled in a predetermined prosthetic site in a human body to form a hardened calcium phosphate/collagen composite.

18 Claims, 3 Drawing Sheets

(56) References Cited

FOREIGN PATENT DOCUMENTS

| JP | 2001-170160 | 6/2001 |
|----|-------------|--------|
| JP | 2005-521440 | 7/2005 |
| JP | 3966539 | 6/2007 |
| WO | 02/36518 | 5/2002 |
| WO | 03/035128 | 5/2003 |
| WO | 2008/026596 | 3/2008 |

OTHER PUBLICATIONS

English language Abstract for JP 2003-020261, Jan. 24, 2003, corresponding to JP 3966539.

Fig. 5

CALCIUM PHOSPHATE CEMENT COMPOSITION AND ITS KIT FOR BONE PROSTHESIS

FIELD OF THE INVENTION

The present invention relates to a calcium phosphate cement composition for bone prosthesis fit into a prosthetic site having an arbitrary shape, and having excellent capability of being absorbed and substituted with autogenous bones, and its kit.

BACKGROUND OF THE INVENTION

With high affinity for autogenous bones, calcium phosphate is used as a prosthesis material for bones and teeth injected into a predetermined site in a human body in plastic surgery, neurological surgery, plastic and reconstructive surgery, oral surgery, etc. The methods of using calcium phosphate-based bone prosthesis materials include (1) a method of embedding a sintered body of calcium phosphate powder in a predetermined site in a human body, and (2) a method of injecting a paste-like mixture obtained by blending a calcium phosphate cement with an aqueous hardening liquid into a predetermined site in a human body, and hardening it. In the method (2), because the bone prosthesis material has a high degree of shape freedom, it can be easily fit into a prosthetic site having an arbitrary shape.

As bone prosthesis materials used in the method (2), various calcium phosphate cements have been proposed. For instance, JP 5-23387 A proposes a calcium phosphate cement capable of forming a hardened porous body, which comprises (a) a powdery agent comprising α-type tribasic calcium phosphate and dibasic calcium phosphate, a molar ratio of Ca/P being 1.40-1.498, (b) polylactic acid powder, and (c) an aqueous liquid agent. However, polylactic acid has such high crystallinity that it does not have a sufficient decomposition speed in a living body. Accordingly, this hardened calcium phosphate cement has insufficient capability of being absorbed and substituted with autogenous bones.

Japanese Patent 3966539 discloses a quick-hardening, living-bone-reinforcing calcium phosphate cement comprising 5-500 ppm of bone morphogenetic proteins, 0.03-2% by mass of magnesium phosphate, and 5-35% by mass of dibasic calcium phosphate, the balance being tetrabasic calcium phosphate and inevitably contained hydroxyapatite, the bone morphogenetic proteins being carried on dibasic calcium phosphate surfaces. However, because a hardened body of this calcium phosphate cement does not contain an apatite/collagen composite, it has insufficient capability of being absorbed and substituted with autogenous bones.

WO 02/36518 A1 discloses a self-hardening bone cement kit comprising a liquid agent containing a first reaction component (sodium phosphate), acid such as citric acid, and a powdery agent containing second reaction components (a calcium source and a phosphoric acid source) reacted with the first reaction component to form a self-hardening bone cement, the powdery agent comprising carbonate selected from the group consisting of sodium carbonate, sodium hydrogen carbonate, calcium carbonate, calcium hydrogen carbonate and mixtures thereof, a weight ratio of the acid and the carbonate to the first and second reaction components being about 10-20%. However, because this kit does not contain an apatite/collagen composite, it has insufficient capability of being absorbed and substituted with autogenous bones. In addition, because it does not contain a thickener, a carbon dioxide gas generated by the reaction of carbonate and acid is not sufficiently retained in the cement, resulting in as small porosity as about 50% or less.

OBJECT OF THE INVENTION

Accordingly, an object of the present invention is to provide a calcium phosphate cement composition for bone prosthesis, which is fit into a prosthetic site having an arbitrary shape, and has excellent capability of being absorbed and substituted with autogenous bones, and its kit.

DISCLOSURE OF THE INVENTION

As a result of intensive research in view of the above object, the inventor has found that (1) a paste-like mixture obtained by blending calcium phosphate powder and a powdery apatite/collagen composite with water is fit into a prosthetic site having an arbitrary shape, that (2) a hardened calcium phosphate/collagen composite formed therefrom has excellent capability of being absorbed and substituted with autogenous bones, and that (3) a foamed paste-like mixture obtained by adding a powdery foaming agent and a high-concentration thickener sufficiently retains pores because of high viscosity, thereby forming a high-porosity, hardened, porous calcium phosphate/collagen composite. The present invention has been completed based on such findings.

Thus, the calcium phosphate cement composition kit of the present invention comprises (a) 100 parts by mass of calcium phosphate powder, (b) 5-50 parts by mass of a powdery apatite/collagen composite, and (c) 15-50 parts by mass of an aqueous blending liquid, per the total amount (100 parts by mass) of the calcium phosphate powder and the powdery apatite/collagen composite; a paste-like mixture obtained by their blending being filled in a predetermined prosthetic site in a human body to form a hardened calcium phosphate/collagen composite.

The calcium phosphate cement composition kit of the present invention comprises (A) a powdery agent comprising 100 parts by mass of calcium phosphate powder, and 5-50 parts by mass of a powdery apatite/collagen composite, and (B) an aqueous blending liquid; a paste-like mixture obtained by blending the powdery agent with the aqueous blending liquid, in such a proportion that the aqueous blending liquid is 15-50 parts by mass per the total amount (100 parts by mass) of the calcium phosphate powder and the powdery apatite/collagen composite, being filled in a predetermined prosthetic site in a human body to form a hardened calcium phosphate/collagen composite.

The aqueous blending liquid preferably contains a thickener in a concentration of 2.5-12.5% by mass. The thickener is preferably at least one selected from the group consisting of sodium chondroitin sulfate, sodium hyaluronate and carboxymethylcellulose.

In order that the paste-like mixture has a proper hardening time, and that the hardened calcium phosphate/collagen composite has excellent bone absorption/substitution capability (capability of being absorbed and substituted with autogenous bones), the calcium phosphate powder preferably comprises tribasic calcium phosphate powder as a main component. The more preferred composition of the calcium phosphate powder comprises, in addition to the tribasic calcium phosphate powder, 2-10% by mass of dibasic calcium phosphate powder, 10-25% by mass of tetrabasic calcium phosphate powder, 5% or less by mass of other calcium phosphate compound powders than the dibasic to tetrabasic calcium phosphates, and further 0.03-2% by mass of magnesium phosphate powder for improving the fluidity of the paste-like mixture. The most preferable composition of the calcium phosphate powder comprises, in addition to the tribasic calcium phosphate powder, 3-7% by mass of dibasic calcium phosphate powder, 15-20% by mass of tetrabasic calcium phosphate powder, and 3% or less by mass of other calcium phosphate compound powders than the dibasic to tetrabasic calcium phosphates, and further 0.05-0.5% by mass of magnesium phosphate powder.

The apatite in the powdery apatite/collagen composite is preferably hydroxyapatite.

The calcium phosphate cement composition preferably further comprises a powdery foaming agent comprising carbonate or hydrogen carbonate and a solid organic acid or its salt in a proportion of 10-50 parts by mass per the total amount (100 parts by mass) of the calcium phosphate powder and the powdery apatite/collagen composite. In the case of the calcium phosphate cement composition kit, the powdery agent comprises the powdery foaming agent.

The carbonate is preferably at least one selected from the group consisting of sodium carbonate, potassium carbonate, magnesium carbonate, calcium carbonate and ammonium carbonate. The hydrogen carbonate is preferably at least one selected from the group consisting of sodium hydrogen carbonate, potassium hydrogen carbonate, magnesium hydrogen carbonate, calcium hydrogen carbonate and ammonium hydrogen carbonate. Among them, sodium hydrogen carbonate is most preferable.

The solid organic acid is preferably at least one selected from the group consisting of solid aliphatic carboxylic acids, solid aliphatic hydroxycarboxylic acids, ascorbic acid, aspartic acid and glutamic acid. Among them, citric acid is most preferable.

The thickener is preferably at least one selected from the group consisting of sodium chondroitin sulfate, sodium hyaluronate and carboxymethylcellulose.

The calcium phosphate cement composition preferably further comprises 2-10 parts by mass of a hardening accelerator, per 100 parts by mass of the calcium phosphate powder. In the case of the calcium phosphate cement composition kit, the hardening accelerator is preferably added to the aqueous blending liquid. The hardening accelerator is preferably at least one selected from the group consisting of sodium lactate, disodium succinate, sodium phosphate and sodium chloride.

The calcium phosphate cement composition according to one preferred embodiment of the present invention comprises (a) 100 parts by mass of calcium phosphate powder, (b) 5-50 parts by mass of a powdery apatite/collagen composite per 100 parts by mass of the calcium phosphate powder, (c) 10-50 parts by mass of a powdery foaming agent comprising carbonate or hydrogen carbonate and a solid organic acid or its salt, per the total amount (100 parts by mass) of the calcium phosphate powder and the powdery apatite/collagen composite, and (d) 15-50 parts by mass of an aqueous blending liquid, per the total amount (100 parts by mass) of the calcium phosphate powder and the powdery apatite/collagen composite, the aqueous blending liquid containing a thickener in a concentration of 2.5-12.5% by mass; a foamed paste-like mixture obtained by their blending being filled in a predetermined prosthetic site in a human body to form a hardened, porous calcium phosphate/collagen composite.

The calcium phosphate cement composition kit according to another preferred embodiment of the present invention comprises (A) a powdery agent comprising (a) 100 parts by mass of calcium phosphate powder, (b) 5-50 parts by mass of a powdery apatite/collagen composite per 100 parts by mass of the calcium phosphate powder, and (c) 10-50 parts by mass of a powdery foaming agent comprising carbonate or hydrogen carbonate and a solid organic acid or its salt, per the total amount (100 parts by mass) of the calcium phosphate powder and the powdery apatite/collagen composite, and (B) an aqueous blending liquid containing a thickener in a concentration of 2.5-12.5% by mass; a paste-like mixture obtained by blending the powdery agent with the aqueous blending liquid, in such a proportion that the aqueous blending liquid is 15-50 parts by mass per the total amount (100 parts by mass) of the calcium phosphate powder and the powdery apatite/collagen composite, being filled in a predetermined prosthetic site in a human body to form a hardened, porous calcium phosphate/collagen composite.

DESCRIPTION OF THE PREFERRED EMBODIMENTS

[1] Calcium Phosphate Cement Composition
(1) Calcium Phosphate Powder

The calcium phosphate powder, which is hardened by a hydration reaction to form a porous body, preferably comprises tribasic calcium phosphate (tricalcium phosphate) powder as a main component. The more preferred composition of the calcium phosphate powder comprises, per 100% by mass of the entire calcium phosphate powder, 2-10% by mass of dibasic calcium phosphate (calcium hydrogen phosphate) powder, 10-25% by mass of tetrabasic calcium phosphate (tetracalcium phosphate) powder, and 5% or less by mass of the other calcium phosphate compound powders than the dibasic to tetrabasic calcium phosphates, the balance being tribasic calcium phosphate powder. The calcium phosphate powder preferably further comprises 0.03-2% by mass of magnesium phosphate powder. Each component powder may be anhydride or hydrate, and when the hydrate powder is used, its amount is expressed by an amount as anhydride.

(a) Tribasic Calcium Phosphate

Tribasic calcium phosphate, a main component, is preferably of an α type, but it may be a mixture of an α type and a β type in a range not hindering the effects of the present invention. The particle size range of the tribasic calcium phosphate powder is preferably about 0.1-500 μm, more preferably about 1-100 μm. The average particle size of the tribasic calcium phosphate powder is preferably about 1-50 μm, more preferably about 2-10 μm. The amount of the tribasic calcium phosphate powder is preferably 60% or more by mass, more preferably 65% or more by mass, most preferable 70% or more by mass, per 100% by mass of the entire calcium phosphate powder.

(b) Dibasic Calcium Phosphate

The dibasic calcium phosphate has a function of accelerating hardening. The particle size range and average particle size of the dibasic calcium phosphate powder may be the same as those of the tribasic calcium phosphate powder. To obtain a proper hardening time, the amount of the dibasic calcium phosphate powder is preferably 2-10% by mass, more preferably 3-7% by mass, per 100% by mass of the entire calcium phosphate powder.

(c) Tetrabasic Calcium Phosphate

The tetrabasic calcium phosphate has a function of accelerating the absorption and substitution of the hardened calcium phosphate/collagen composite to an autogenous bone. The particle size range and average particle size of tetrabasic calcium phosphate may be the same as those of the tribasic calcium phosphate powder. In order that the hardened calcium phosphate/collagen composite has sufficient bone absorption/substitution capability and strength, the amount of the tetrabasic calcium phosphate powder is preferably 10-25% by mass, more preferably 15-20% by mass, per 100% by mass of the entire calcium phosphate powder.

(d) Other Calcium Phosphate Compounds than Dibasic to Tetrabasic Calcium Phosphates Other calcium phosphate compound powders than the dibasic to tetrabasic calcium phosphates, which are inevitably contained, include, for example, hydroxyapatite powder. The particle size range and average particle size of this calcium phosphate compound powder may be the same as those of the tribasic calcium phosphate powder. The amount of this calcium phosphate compound powder is preferably 5% or less by mass, more preferably 3% or less by mass, per 100% by mass of the entire calcium phosphate powder.

(e) Magnesium Phosphate

The magnesium phosphate is preferably tribasic magnesium phosphate (trimagnesium phosphate), but it may contain, in addition to tribasic magnesium phosphate, other magnesium phosphates such as monobasic magnesium phosphate (magnesium dihydrogen phosphate), dibasic magnesium phosphate (magnesium hydrogen phosphate), magnesium pyrophosphate, etc., in a range not hindering the effects of the present invention. The particle size range and average particle size of the magnesium phosphate powder may be the same as those of the tribasic calcium phosphate powder. In order that a paste-like mixture of the calcium phosphate powder has good fluidity, the amount of the magnesium phosphate powder is preferably 0.03-2% by mass, more preferably 0.05-0.5% by mass, per 100% by mass of the entire calcium phosphate powder.

(2) Powdery Apatite/Collagen Composite

The apatite/collagen composite has a structure similar to that of a living bone, in which hydroxyapatite is dispersed in collagen. The C-axis of hydroxyapatite is preferably aligned with collagen fibers. Namely, the apatite/collagen composite is preferably self-organized. Also, the apatite/collagen composite is porous, with elasticity after water absorption.

The mass ratio of collagen to hydroxyapatite is preferably 1/9-4/6, more preferably 1.5/8.5-3/7, particularly about 2/8. The particle size distribution of the powdery apatite/collagen composite is preferably in a range of about 10 µm to about 2,000 µm, more preferably in a range of about 30 µm to about 1,000 µm. To obtain excellent capability of being absorbed and substituted with autogenous bones, the amount of the powdery apatite/collagen composite is preferably 5-50 parts by mass, more preferably 10-40 parts by mass, per 100 parts by mass of the calcium phosphate powder. The powdery apatite/collagen composite can be produced by the following method.

(a) Starting Materials

Starting materials for the powdery apatite/collagen composite are collagen, phosphoric acid or its salts (simply called "phosphoric acid (salt)" below), and calcium salts. The collagen is preferably extracted from animals, though their kinds, tissue parts, etc. are not particularly restrictive. For example, collagen obtained from skins, bones, cartilages, tendons, internal organs, etc. of mammals such as cow, pig, horse, rabbit and rat, and birds such as hen, etc., and skins, bones, cartilages, fins, scales, internal organs, etc. of fish such as cod, flounder, flatfish, salmon, trout, tuna, mackerel, red snapper, sardine, shark, etc. may be used. Collagen produced by gene recombination technologies may also be used.

The phosphoric acid (salt) may be phosphoric acid, disodium hydrogen phosphate, sodium dihydrogen phosphate, dipotassium hydrogen phosphate, potassium dihydrogen phosphate, etc. The calcium salts may be calcium carbonate, calcium acetate, calcium hydroxide, etc. The phosphoric acid (salt) and the calcium salt are preferably used in the form of a uniform aqueous solution or suspension.

(b) Preparation of Solution

In an aqueous solution of collagen and phosphoric acid (salt) [aqueous collagen/phosphoric acid (salt) solution], the concentration of collagen is preferably 0.1-1.5% by mass, more preferably 0.1-1% by mass, and the concentration of phosphoric acid (salt) is preferably 15-240 mM, more preferably 20-150 mM. The concentration of the aqueous calcium salt solution or suspension is preferably 50-800 mM, more preferably 300-500 mM. By adjusting the concentrations of the aqueous collagen/phosphoric acid (salt) solution and the aqueous calcium salt solution or suspension, the fiber length of the apatite/collagen composite can be controlled. Specifically, the higher concentration each solution has, the shorter fibers are obtained, and vice versa.

(c) Production of Apatite/Collagen Composite

The aqueous collagen/phosphoric acid (salt) solution and the aqueous calcium salt solution or suspension are simultaneously dropped into water substantially in the same amount as that of the aqueous calcium salt solution or suspension at room temperature, to form an apatite/collagen composite. The fiber length of the apatite/collagen composite can be controlled by adjusting dropping conditions. The dropping speed of each solution is preferably 1 to 60 mL/minute, more preferably about 30 mL/minute. The stirring speed is preferably 1-400 rpm, more preferably about 200 rpm.

The mass ratio of the phosphoric acid (salt) to the calcium salt is preferably 1/1 to 2/5. The mass ratio of collagen to the total of the phosphoric acid (salt) and the calcium salt is preferably 1/9 to 4/6, more preferably 1.5/8.5 to 3/7, particularly about 2/8.

The reaction solution is preferably kept at pH of 8.9 to 9.1 by maintaining the concentration of calcium ions at 3.75 mM or less and the concentration of phosphoric ions at 2.25 mM or less in the reaction solution. Outside the above concentration ranges of calcium ions and phosphoric ions, the self-organization of the composite would be hindered. The above conditions provide the fibrous apatite/collagen composite with average length of 2 mm or less.

(d) Production of Powder

The fibrous apatite/collagen composite can be turned to powder by a freeze-drying method or a granulation method.

(i) Freeze-Drying Method

The fibrous apatite/collagen composite is dispersed in a solvent such as water, etc. to form a suspension. The volume ratio of the fibrous apatite/collagen composite to the solvent is preferably 5/95-1/99. This suspension is sprayed into a liquid (for example, liquid nitrogen) or a gas at $-150°$ C. to $-250°$ C.

by a spray drier, etc. to carry out its freeze-drying, and then cross-linked by a thermal dehydration treatment in vacuum, for example, at 140° C. for 12 hours, or by a treatment with an agent such as glutaraldehyde, etc. As a result, the fibrous apatite/collagen composite is agglomerated to substantially spherical, powdery apatite/collagen composite. The particle size of the powdery apatite/collagen composite can be controlled by changing the freezing temperature, the spraying conditions, etc. Hydroxyapatite in the powdery apatite/collagen composite has low crystallinity because of no thermal hysteresis at high temperatures.

(ii) Granulation Method

The fibrous apatite/collagen composite is blended with a solvent such as water, etc. The mass ratio of the fibrous apatite/collagen composite to the solvent is preferably 0.5/1 to 1/1. The resultant blend is granulated by a wet-extrusion granulator, etc. The resultant granules having cylindrical shapes with uneven lengths are preferably spheroidized by a spheroidizing machine. The resultant spherical particles are dried, and cross-linked by thermal dehydration in vacuum or by a treatment with an agent such as glutaraldehyde, etc., to obtain substantially spherical, powdery apatite/collagen composite. Their particle sizes can be controlled by adjusting the screen mesh in the granulator. Hydroxyapatite in the powdery apatite/collagen composite also has low crystallinity.

(3) Powdery Foaming Agent

To obtain the hardened, porous calcium phosphate/collagen composite, the calcium phosphate cement composition preferably contains a powdery foaming agent. The powdery foaming agent comprises carbonate or hydrogen carbonate and a solid organic acid or its salt. The carbonate or hydrogen carbonate generates a carbon dioxide gas by a neutralization reaction with the solid organic acid or its salt. The carbonates or hydrogen carbonates preferably include carbonates or hydrogen carbonates of alkali metals or alkaline earth metals, for example, sodium carbonate, potassium carbonate, magnesium carbonate, calcium carbonate, sodium hydrogen carbonate, potassium hydrogen carbonate, magnesium hydrogen carbonate, calcium hydrogen carbonate, etc. Ammonium carbonate and ammonium hydrogen carbonate may also be used. Among them, sodium hydrogen carbonate is most preferable.

The solid organic acids include solid aliphatic carboxylic acids, solid aliphatic hydroxycarboxylic acids, ascorbic acid, aspartic acid, glutamic acid, etc. The solid organic acid salts include their sodium salts, potassium salts, etc.

The solid aliphatic carboxylic acids may be either saturated or unsaturated; the solid saturated aliphatic carboxylic acids include capric acid, palmitic acid, margaric acid, malonic acid, succinic acid, glutaric acid, adipic acid, pimelic acid, suberic acid, azelaic acid, sebacic acid, etc., and the solid unsaturated aliphatic carboxylic acids include fumaric acid, maleic acid, aconitic acid, oleic acid, linoleic acid, linolenic acid, etc. The solid aliphatic hydroxycarboxylic acids may be either saturated or unsaturated, including glycolic acid, lactic acid, hydroxybutyric acid, malic acid, tartaric acid, carboxymethyltartaric acid, hydroxycaproic acid, citric acid, gluconic acid, galacturonic acid, glucuronic acid, mannuronic acid, etc. Among them, citric acid is most preferable.

For example, in the case of a combination of sodium hydrogen carbonate and citric acid, a carbon dioxide gas is generated by the following reaction.

Sodium hydrogen carbonate is a monovalent base, while citric acid is a trivalent acid. Accordingly, when they are mixed at a molar ratio of 3:1, a neutralization reaction occurs stoichiometrically. Namely, the chemical equivalent ratio of sodium hydrogen carbonate to citric acid is preferably substantially 1, though there would be no problems even if sodium hydrogen carbonate were slightly excessive. This molar ratio is applicable to general carbonates and solid organic acids.

To obtain the hardened, porous calcium phosphate/collagen composite having proper communicating pores, the amount of the powdery foaming agent is 10-50 parts by mass, preferably 15-40 parts by mass, more preferably 20-40 parts by mass, per the total amount (100 parts by mass) of the calcium phosphate powder and the powdery apatite/collagen composite.

(4) Aqueous Blending Liquid

The powdery foaming agent and water cause a neutralization reaction to generate a carbon dioxide gas, so that the calcium phosphate powder is turned to a foamed, paste-like mixture. To make the paste-like mixture highly viscous to retain pores in the paste, the amount of the aqueous blending liquid is 15-50 parts by mass, preferably 20-40 parts by mass, more preferably 25-38 parts by mass, per the total amount (100 parts by mass) of the calcium phosphate powder and the powdery apatite/collagen composite.

(a) Thickener

The thickeners include mucopolysaccharides such as sodium chondroitin sulfate and sodium hyaluronate, and high-molecular-weight compounds such as carboxymethylcellulose, etc. They may be added alone or in combination. The concentration of the thickener is determined, such that a carbon dioxide gas generated by the neutralization reaction of carbonate and acid sufficiently remains in the paste, and that the paste has such viscosity that it is not broken by foaming. Taking into consideration the easiness of forming the paste-like mixture, the concentration of the thickener is 2.5-12.5% by mass, preferably 6-12% by mass, more preferably 7-11% by mass. A higher thickener concentration in the aqueous blending liquid provides the paste-like mixture with higher viscosity, resulting in pores well retained in the paste-like mixture while preventing the breakage of the paste by foaming.

(b) Hardening Accelerator

The aqueous blending liquid preferably comprises a hardening accelerator for the calcium phosphate powder. The hardening accelerator may be a water-soluble sodium salt such as sodium lactate, disodium succinate, sodium phosphate, sodium chloride, etc. They may be used alone or in combination. The amount of the hardening accelerator is preferably 2-10 parts by mass, more preferably 3-7 parts by mass, most preferable 4-6 parts by mass, per 100 parts by mass of the calcium phosphate powder.

[2] Calcium Phosphate Cement Composition Kit

The calcium phosphate cement composition kit comprises (A) a powdery agent comprising 100 parts by mass of calcium phosphate powder, and 5-50 parts by mass of a powdery apatite/collagen composite, and (B) an aqueous blending liquid. When the hardened, porous calcium phosphate/collagen composite is produced, the powdery agent further comprises 10-50 parts by mass of a powdery foaming agent comprising carbonate or hydrogen carbonate and a solid organic acid or its salt, per the total amount (100 parts by mass) of the calcium phosphate powder and the powdery apatite/collagen composite. The aqueous blending liquid preferably contains a thickener in a concentration of 2.5-12.5% by mass, and further a hardening accelerator for the calcium phosphate powder.

In the case of a kit for producing the hardened, porous calcium phosphate/collagen composite, the existence of the powdery foaming agent comprising carbonate or hydrogen carbonate and a solid organic acid or its salt in the powdery agent makes a ratio of carbonate or hydrogen carbonate to a solid organic acid or its salt invariable depending on the ratio of the powdery agent to the aqueous blending liquid. Accordingly, at any viscosity of the paste-like mixture, a neutralization reaction occurs completely between carbonate or hydrogen carbonate and a solid organic acid or its salt.

For example, when the powdery agent comprising the calcium phosphate powder, the powdery apatite/collagen composite and the powdery foaming agent is blended with the aqueous blending liquid containing a thickener to cause the hydration and hardening reaction of the calcium phosphate powder and the neutralization reaction of the powdery foaming agent simultaneously, a paste-like mixture having relatively high viscosity is obtained by the thickener in the aqueous blending liquid, resulting in a porous body having sufficient strength despite high porosity. The ratio of the powdery agent to the aqueous blending liquid is determined such that the resultant paste-like mixture has desired viscosity and fluidity.

The powdery agent and the aqueous blending liquid at a desired ratio are blended, for instance, by a spatula in a mortar. The resultant paste-like mixture is injected into a predetermined bone prosthetic site in a human body, using a syringe. Because the paste-like mixture is hardened in about 10 minutes, blending and injection should be completed within several minutes. When the paste-like mixture has high viscosity, a high-pressure syringe pump is used.

[3] Properties of Hardened Calcium Phosphate/Collagen Composite

The hardened calcium phosphate/collagen composite obtained from the calcium phosphate cement composition of the present invention has a skeleton constituted by hydroxyapatite $[Ca_{10}(PO_4)_6.(OH)_2]$ crystals formed by the hydration reaction of the calcium phosphate powder, and contains the apatite/collagen composite having excellent affinity for bone tissues. Accordingly, it has excellent capability of being absorbed and substituted with autogenous bones. However, a small amount of α-type tribasic calcium phosphate (α-TCP) may remain in the hardened calcium phosphate/collagen composite. While hydroxyapatite keeps its shape in a living body for a certain period of time, α-TCP is easily dissolved in a living body, inducing bone regeneration. Because too much α-TCP provides the hardened calcium phosphate/collagen composite with too small strength, and because α-TCP is rapidly dissolved in a living body, the amount of the remaining α-TCP is preferably as small as possible. For example, in an X-ray diffraction pattern, a main peak of α-TCP is preferably 0.5-5%, more preferably 0.5-3% of the main peak of hydroxyapatite.

The hardened, porous calcium phosphate/collagen composite obtained by using the foaming agent has communicating pores with as wide a pore size range (pore size distribution) as about 1000 μm or less, with many communicating pores having a pore diameter range of about 5-1000 μm, particularly about 10-800 μm, in which cells (hematopoietic cells, stem cells, etc.) and bone morphogenetic proteins (bone-forming proteins, fibroblast growth factors, etc.) can easily enter and be fixed. The average pore diameter of communicating pores is about 50-500 μm, particularly about 100-400 μm. The pore diameter distribution and average pore diameter of communicating pores can be determined by the image analysis of a scanning electron photomicrograph.

The porosity of the hardened, porous calcium phosphate/collagen composite obtained when the foaming agent is used is 60% or more, preferably 65-95%, particularly 70-90%. When the aqueous blending liquid contains a thickener, the resultant paste-like mixture has high viscosity, so that the hardened, porous calcium phosphate/collagen composite has sufficient self-supportability even if it has as high porosity as up to 95%. With the porosity of less than 60%, sufficient cells and bone morphogenetic proteins do not enter the hardened, porous calcium phosphate/collagen composite, failing to achieve large osteogenic capacity. Because larger porosity provides smaller mechanical strength to the hardened, porous calcium phosphate/collagen composite, the percentage of the aqueous blending liquid is determined to obtain optimum porosity.

In the hardened, porous calcium phosphate/collagen composite having communicating pores having the above pore diameter distribution and average pore diameter, as well as the above porosity, cells and bone morphogenetic proteins easily enter and are fixed, resulting in rapid bone regeneration.

The present invention will be explained in further detail by Examples below without intention of restricting the present invention thereto.

EXAMPLE 1

(1) Production of Fibrous Apatite/Collagen Composite 412 g of an aqueous collagen solution containing phosphoric acid (0.97% by mass of collagen, and 20 mM of phosphoric acid) was added to 400 ml of a 120-mM aqueous phosphoric acid solution, and stirred to obtain a solution I. 400 ml of a 400-mM calcium hydroxide solution (solution II) was also prepared. Both solutions I and II were simultaneously dropped at a speed of 30 mL/min into a vessel containing 200 ml of water (25° C.), to obtain a slurry containing a fibrous apatite/collagen composite. The reaction solution was stirred at 200 rpm during dropping. The reaction solution had pH of 8.9-9.1 during dropping.

(2) Production of Powdery Apatite/Collagen Composite

The slurry was mixed with water to a water content of 95% by volume, to prepare a suspension of the fibrous apatite/collagen composite. This suspension was sprayed into liquid nitrogen by a spray drier, freeze-dried, and then cross-linked by a thermal dehydration treatment in vacuum at 140° C. for 12 hours, to obtain a powdery apatite/collagen composite. SEM observation revealed that the powdery apatite/collagen composite was constituted by spherical particles having a particle size distribution in a range of 30-1000 μm.

(3) Production of Hardened Composite 3.0 g of calcium phosphate powder comprising 5% by mass of dibasic calcium phosphate, 18% by mass of tetrabasic calcium phosphate, 74.9% by mass of tribasic calcium phosphate, 2% by mass of hydroxyapatite and 0.1% by mass of magnesium phosphate was mixed with 1.0 g of the above powdery apatite/collagen composite, 0.5 g of sodium hydrogen carbonate, and 0.5 g of citric acid, to prepare 5.0 g of a powdery agent. Also prepared was 2 mL of an aqueous blending liquid containing sodium chondroitin sulfate in a concentration of 7.0% by mass, and disodium succinate anhydride in a concentration of 15.0% by mass.

Figure 1:
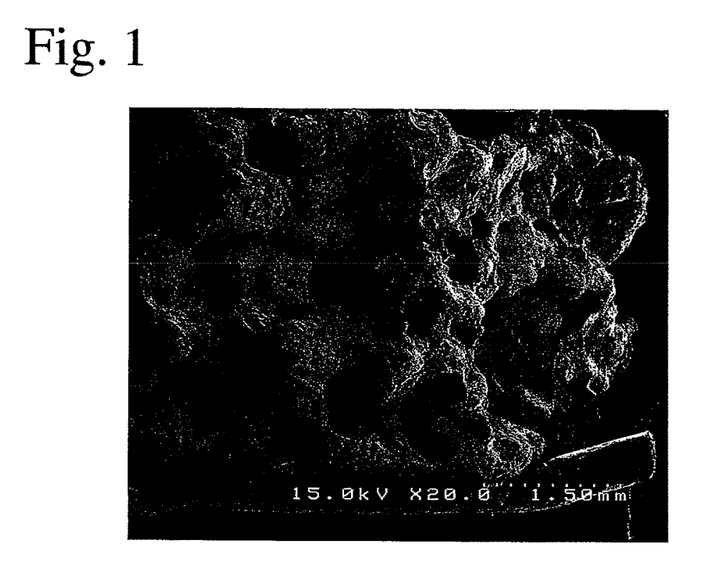
FIG. 1 is a scanning electron photomicrograph (magnification: 20 times) of the hardened, porous calcium phosphate/collagen composite of Example 1.
Figure 2:
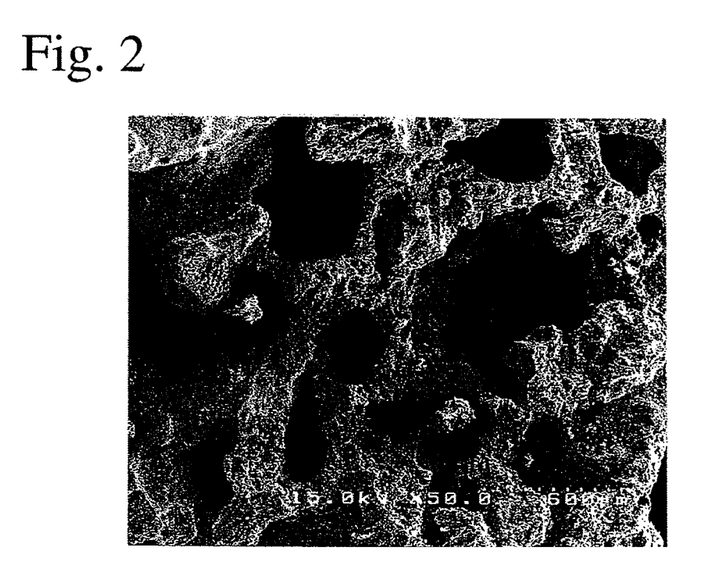
FIG. 2 is a scanning electron photomicrograph (magnification: 50 times) of the hardened, porous calcium phosphate/collagen composite of Example 1.
Figure 3:
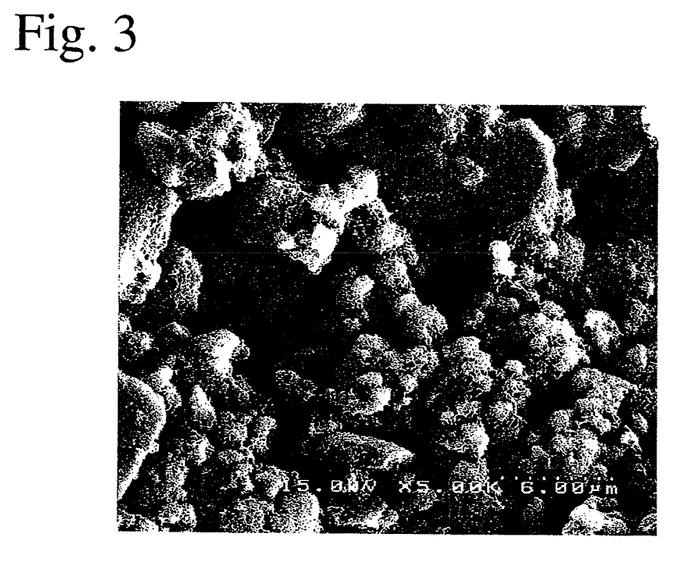
FIG. 3 is a scanning electron photomicrograph (magnification: 5,000 times) of the hardened, porous calcium phosphate/collagen composite of Example 1.

A paste-like mixture obtained by mixing the above powdery agent and the above an aqueous blending liquid was smoothly extruded from a syringe needle. The extruded paste-like mixture was foamed and hardened at room temperature, resulting in a hardened porous calcium phosphate/collagen composite after 10 minutes. The scanning electron photomicrographs of the hardened porous calcium phosphate/collagen composite are shown in FIGS. 1-3. As is clear from FIGS. 1 and 2, the hardened, porous calcium phosphate/collagen composite had communicating pores formed by the foaming agent, with porosity of 85%. The pore size distribution and average pore size of communicating pores determined from these photographs were 300-700 μm and 500 μm, respectively. As is clear from FIG. 3, the hardened, porous calcium phosphate/collagen composite had a structure, in which the powdery apatite/collagen composite was bonded by hydroxyapatite formed by the reaction of the calcium phosphate powder.

EXAMPLE 2

Figure 4:
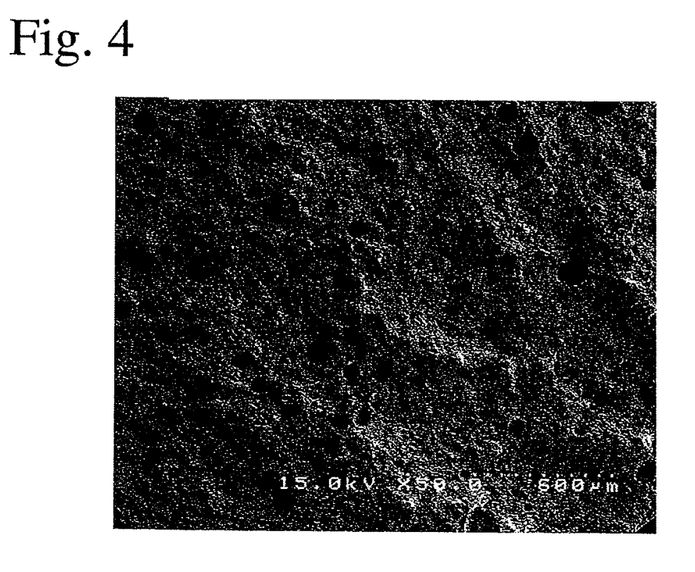
FIG. 4 is a scanning electron photomicrograph (magnification: 50 times) of the hardened calcium phosphate/collagen composite of Example 2.
Figure 5:
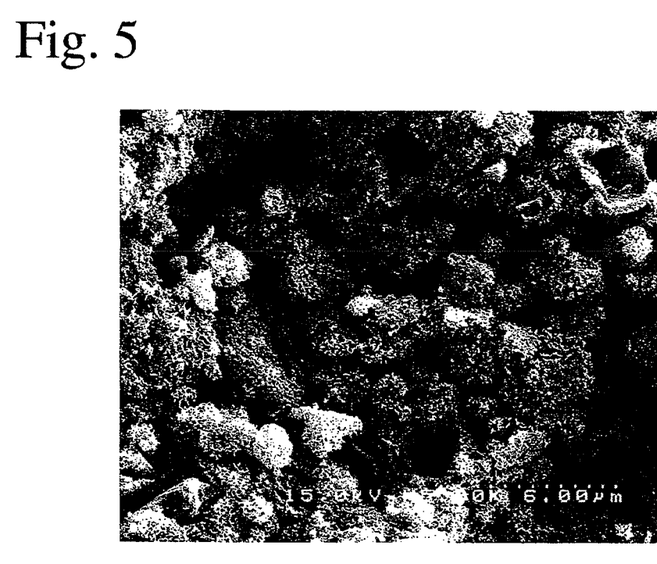
FIG. 5 is a scanning electron photomicrograph (magnification: 5,000 times) of the hardened calcium phosphate/collagen composite of Example 2.

A hardened calcium phosphate/collagen composite was produced in the same manner as in Example 1, except for using no sodium hydrogen carbonate and no citric acid. The scanning electron photomicrographs of the hardened calcium phosphate/collagen composite are shown in FIGS. 4 and 5. This hardened calcium phosphate/collagen composite had porosity of 60%, with a structure in which the powdery apatite/collagen composite was bonded by hydroxyapatite formed by the reaction of the calcium phosphate powder.

EXAMPLE 3

A hardened, porous calcium phosphate/collagen composite was produced in the same manner as Example 1, except that the amount of sodium chondroitin sulfate was 10% by mass. A paste-like mixture formed by the powdery agent and the aqueous blending liquid was highly viscous, and hardened while being foamed after 10 minutes. The resultant hardened, porous calcium phosphate/collagen composite had a large number of communicating pores, with porosity of 90%.

EFFECTS OF THE INVENTION

A paste-like mixture formed from the calcium phosphate cement composition comprising the calcium phosphate powder and the powdery apatite/collagen composite is well fit into a prosthetic site having an arbitrary shape, so that it becomes a hardened calcium phosphate/collagen composite having excellent capability of being absorbed and substituted with an autogenous bone. Further, when a powdery foaming agent comprising carbonate or hydrogen carbonate and a solid organic acid or its salt is added to the calcium phosphate cement composition, the resultant hardened calcium phosphate/collagen composite have communicating pores having such proper diameters that cells and bone morphogenetic proteins can easily enter and be fixed, exhibiting excellent capability of being absorbed and substituted with autogenous bones.

Using the calcium phosphate cement composition kit of the present invention, a paste-like mixture with desired fluidity and viscosity can be obtained simply by blending the powdery agent and the aqueous blending liquid at an operation site, and a hardened calcium phosphate/collagen composite can be easily shaped such that it is fit into a prosthetic site having an arbitrary shape, with little burden on a human body during the prosthetic process. Also, the hardened calcium phosphate/collagen composite made porous by the powdery foaming agent has better capability of being absorbed and substituted with autogenous bones. The calcium phosphate cement composition and its kit having such features according to the present invention are suitable as bone prosthesis materials, for example, for curing bone defects or cavities, curing broken bones, assisting the fixing of broken bones, fixing metal screws for bonding bones, filling gaps between artificial joints and bones.

What is claimed is:

1. A calcium phosphate cement composition comprising (a) 100 parts by mass of calcium phosphate powder, (b) 5-50 parts by mass of a powdery apatite/collagen composite, (c) 15-50 parts by mass of an aqueous blending liquid, and (d) 10-50 parts by mass of a powdery foaming agent comprising carbonate or hydrogen carbonate and a solid organic acid or its salt, per the total amount (100 parts by mass) of the calcium phosphate powder and the powdery apatite/collagen composite; a pasty mixture obtained by their blending being filled in a prosthetic site in a human body to form a hardened calcium phosphate/collagen composite.

2. The calcium phosphate cement composition according to claim 1, wherein the aqueous blending liquid contains a thickener in a concentration of 2.5-12.5% by mass.

3. The calcium phosphate cement composition according to claim 1, further comprising 2-10 parts by mass of a hardening accelerator per 100 parts by mass of the calcium phosphate powder.

4. The calcium phosphate cement composition according to claim 1, wherein the calcium phosphate powder comprises tribasic calcium phosphate as a main component.

5. The calcium phosphate cement composition according to claim 4, wherein the calcium phosphate powder comprises, in addition to the tribasic calcium phosphate, 2-10% by mass of dibasic calcium phosphate, 10-25% by mass of tetrabasic calcium phosphate, 5% or less by mass of other calcium phosphate compounds than the dibasic to tetrabasic calcium phosphates, and 0.03-2% by mass of magnesium phosphate.

6. The calcium phosphate cement composition according to claim 1, wherein apatite in the powdery apatite/collagen composite is hydroxyapatite.

7. The calcium phosphate cement composition according to claim 1, wherein the carbonate is at least one selected from the group consisting of sodium carbonate, potassium carbonate, magnesium carbonate, calcium carbonate and ammonium carbonate, the hydrogen carbonate is at least one selected from the group consisting of sodium hydrogen carbonate, potassium hydrogen carbonate, magnesium hydrogen carbonate, calcium hydrogen carbonate and ammonium hydrogen carbonate, and the solid organic acid is at least one selected from the group consisting of solid aliphatic carboxylic acids, solid aliphatic hydroxycarboxylic acids, ascorbic acid, aspartic acid and glutamic acid.

8. The calcium phosphate cement composition according to claim 2, wherein the thickener is at least one selected from the group consisting of sodium chondroitin sulfate, sodium hyaluronate and carboxymethylcellulose.

9. The calcium phosphate cement composition according to claim 3, wherein the hardening accelerator is at least one selected from the group consisting of sodium lactate, disodium succinate, sodium phosphate and sodium chloride.

10. A calcium phosphate cement composition kit comprising (A) a powdery agent comprising 100 parts by mass of calcium phosphate powder, 5-50 parts by mass of a powdery apatite/collagen composite, and a powdery foaming agent comprising carbonate or hydrogen carbonate and a solid organic acid or its salt, in a proportion of 10-50 parts by mass per the total amount (100 parts by mass) of the calcium phosphate powder and the powdery apatite/collagen composite, and (B) an aqueous blending liquid; a paste-like mixture being obtained by blending the powdery agent with the aqueous blending liquid, in such a proportion that the aqueous blending liquid is 15-50 parts by mass per the total amount (100 parts by mass) of the calcium phosphate powder and the powdery apatite/collagen composite, and filled in a predetermined prosthetic site in a human body to form a hardened calcium phosphate/collagen composite.

11. The calcium phosphate cement composition kit according to claim 10, wherein the aqueous blending liquid contains a thickener in a concentration of 2.5-12.5% by mass.

12. The calcium phosphate cement composition kit according to claim 11, wherein the aqueous blending liquid further comprises 2-10 parts by mass of a hardening accelerator per 100 parts by mass of the calcium phosphate powder.

13. The calcium phosphate cement composition kit according to claim 10, wherein the calcium phosphate powder comprises tribasic calcium phosphate as a main component.

14. The calcium phosphate cement composition kit according to claim 13, wherein the calcium phosphate powder comprises, in addition to the tribasic calcium phosphate, 2-10% by mass of dibasic calcium phosphate, 10-25% by mass of tetrabasic calcium phosphate, 5% or less by mass of other calcium phosphate compounds than the dibasic to tetrabasic calcium phosphates, and 0.03-2% by mass of magnesium phosphate.

15. The calcium phosphate cement composition kit according to claim 10, wherein apatite in the powdery apatite/collagen composite is hydroxyapatite.

16. The calcium phosphate cement composition kit according to claim 10, wherein the carbonate is at least one selected from the group consisting of sodium carbonate, potassium carbonate, magnesium carbonate, calcium carbonate and ammonium carbonate, the hydrogen carbonate is at least one selected from the group consisting of sodium hydrogen carbonate, potassium hydrogen carbonate, magnesium hydrogen carbonate, calcium hydrogen carbonate and ammonium hydrogen carbonate, and the solid organic acid is at least one selected from the group consisting of solid aliphatic carboxylic acids, solid aliphatic hydroxycarboxylic acids, ascorbic acid, aspartic acid and glutamic acid.

17. The calcium phosphate cement composition kit according to claim 11, wherein the thickener is at least one selected from the group consisting of sodium chondroitin sulfate, sodium hyaluronate and carboxymethylcellulose.

18. The calcium phosphate cement composition kit according to claim 12, wherein the hardening accelerator is at least one selected from the group consisting of sodium lactate, disodium succinate, sodium phosphate and sodium chloride.

* * * * *